(12) United States Patent
Shinoka et al.

(10) Patent No.: US 8,372,433 B2
(45) Date of Patent: Feb. 12, 2013

(54) SUBSTRATE FOR CULTURE OF CARDIOVASCULAR TISSUE

(75) Inventors: Toshiharu Shinoka, Tokyo (JP); Goki Matsumura, Tokyo (JP); Yoshito Ikada, Kyoto (JP); Shojiro Matsuda, Kyoto (JP); Yuki Sakamoto, Kyoto (JP); Tsuguyoshi Taira, Kyoto (JP)

(73) Assignee: Gunze Limited, Kyoto (JP)

( * ) Notice: Subject to any disclaimer, the term of this patent is extended or adjusted under 35 U.S.C. 154(b) by 653 days.

(21) Appl. No.: 12/523,124

(22) PCT Filed: Jan. 18, 2008

(86) PCT No.: PCT/JP2008/050609
§ 371 (c)(1),
(2), (4) Date: Sep. 17, 2009

(87) PCT Pub. No.: WO2008/088042
PCT Pub. Date: Jul. 24, 2008

(65) Prior Publication Data
US 2010/0055781 A1    Mar. 4, 2010

(30) Foreign Application Priority Data
Jan. 18, 2007 (JP) ................................. 2007-009469

(51) Int. Cl.
*C12N 5/00* (2006.01)
(52) U.S. Cl. ........................ 424/484; 424/93.7; 435/395
(58) Field of Classification Search ........................ None
See application file for complete search history.

(56) References Cited

U.S. PATENT DOCUMENTS

| | | |
|---|---|---|
| 5,855,610 A | 1/1999 | Vacanti et al. |
| 5,863,531 A | 1/1999 | Naughton et al. |
| 6,534,084 B1 | 3/2003 | Vyakarnam et al. |
| 2006/0153815 A1 | 7/2006 | Seyda et al. |
| 2007/0282428 A1 | 12/2007 | Igaki |

FOREIGN PATENT DOCUMENTS

| | | |
|---|---|---|
| EP | 0 274 898 | 7/1988 |
| EP | 0 277 678 | 8/1988 |
| EP | 0 528 039 | 2/1993 |
| EP | 0 734 736 | 10/1996 |
| EP | 1 214 952 | 6/2002 |
| JP | 1-230366 | 9/1989 |
| JP | 3-23864 | 1/1991 |
| JP | 6-292716 | 10/1994 |
| JP | 10-234844 | 9/1998 |
| JP | 2001-78750 | 3/2001 |
| JP | 2003-19196 | 1/2003 |
| JP | 2005-34239 | 2/2005 |
| JP | 2005-168760 | 6/2005 |
| JP | 2005-185529 | 7/2005 |
| WO | 96/08213 | 3/1996 |
| WO | 96/38188 | 12/1996 |
| WO | 96/40175 | 12/1996 |
| WO | 2006/051912 | 5/2006 |

OTHER PUBLICATIONS

Shin'oka, et al, "Midterm clinical result of tissue-engineered vascular autografts seeded with autologous bone marrow cells", The Journal of Thoracic and Cardiovascular Surgery, vol. 129, No. 6, 2005, pp. 1330-1338.

Shin'oka, "Clinical Results of Tissue-Engineered Vascular Autografts Seeded with Autologous Bone Marrow Cells", Japan Surgical Society, vol. 105, No. 8, 2004, pp. 459-463 (English abstract on p. 463).

Ichihara, et al., "Clinical Application of Tissue Engineering Graft", Jpn. J. Pediatr. Surg., vol. 36, No. 11, 2004, pp. 1394-1400 (English abstract on p. 1400).

Matsumura, et al., "Successful application of tissue engineered vascular autografts: clinical experience", Biomaterials, vol. 24, No. 13, 2003, pp. 2303-2308.

Inoguchi, et al., "Mechanical responses of a compliant electrospun poly(L-lactide-*co*-ε-caprolactone) small-diameter vascular graft", Biomaterials, vol. 27, No. 8, pp. 1470-1478, 2006.

Matsumura, et al., "Evaluation of Tissue-Engineered Vascular Autografts", Tissue Engineering, vol. 12, No. 11, Nov. 2006, pp. 3075-3083.

Roh, et al., "Construction of an autologous tissue-engineered venous conduit from bone-marrow-derived vascular cells: optimization of cell harvest and seeding techniques", Journal of Pediatric Surgery, vol. 42, No. 1, Jan. 2007, pp. 198-202.

Hibino, et al., "The tissue-engineered vascular graft using bone marrow without culture", The Journal of Thoracic and Cardiovascular Surgery, vol. 129, No. 5, May 2005, pp. 1064-1070.

European Patent Office, Supplementary European Search Report issued in corresponding European Application No. 08703459.1 and mailed Dec. 22, 2009—7 pages.

*Primary Examiner* — Allison Ford
(74) *Attorney, Agent, or Firm* — Hamre, Schumann, Mueller & Larson, P.C.

(57) ABSTRACT

The scaffold for culturing a cardiovascular tissue of the present invention is a scaffold for culturing a cardiovascular tissue, which is tubular, and comprises a foamed polymer comprising a bioabsorbable material reinforced with a reinforcing material comprising a bioabsorbable material, the foamed polymer comprising lactide (D, L, DL isomer)-ε-caprolactone copolymer containing lactide (D, L, DL isomer) in a content of 50 to 54 mole % and ε-caprolactone in a content of 50 to 46 mole %, and the reinforcing material being covered with the foamed polymer.

9 Claims, No Drawings

SUBSTRATE FOR CULTURE OF CARDIOVASCULAR TISSUE

TECHNICAL FIELD

The present invention relates to a scaffold for culturing a cardiovascular tissue, which can regenerate a blood vessel at an extremely high efficiency by cell seeding and transplantation, as well as a method of producing a cardiovascular tissue for transplantation using the same, a method of regenerating a cardiovascular tissue, and a cardiovascular tissue for transplantation.

BACKGROUND ART

Currently, an artificial blood vessel that is most frequently used in the clinical field is an artificial blood vessel using a non-absorbable polymer such as GORE-TEX. Such the artificial blood vessel can exert physical property extremely close to that of a blood vessel, and brings an efficient to some extent in reconstitution of a short-term blood vessel. However, an artificial blood vessel using a non-absorbable polymer has a problem that an anti-coagulant or the like must be continuously administered since a foreign matter remains in a body over a long term after transplantation. In addition, there is also a problem that, when used in infants, it becomes necessary to perform operation again as infants are grown.

On the other hand, in recent years, a tissue regenerating method by so-called regeneration therapy has been tried. Regeneration therapy is a trial attempting to regenerate an autologous tissue by seeding cells constituting a tissue on a cell culturing scaffold that is to be an anchorage, and transplanting this. Regarding the regeneration therapy, many study examples have been reported on a variety of tissues including, for example, a skin (Non-Patent Document 1) and a cartilage (Non-Patent Document 2).

In order to apply such the regeneration therapy to revascularization, the present inventors developed a scaffold for culturing a cardiovascular tissue in which a reinforcing material comprising a bioabsorbable polymer as a core material is incorporated into a foamed polymer comprising a bioabsorbable polymer (Patent Document 1). In this scaffold for culturing a cardiovascular tissue, a foamed polymer functions as an anchorage which can adhere to seeded cells firmly, and the reinforcing material plays a role of providing strength for withstanding a blood flow after transplantation for a term until a blood vessel is regenerated, and also plays a role as a reinforcing material which provides strength for withstanding suturing. Since both of the foamed polymer and the reinforcing material comprise a bioabsorbable polymer, thereby, materials thereof are absorbed after regeneration of a blood vessel, and it becomes unnecessary to continuously use an anti-coagulant or the like. Furthermore, since a regenerated blood vessel is an autologous tissue, growth is also expected. Actually, the scaffold for culturing a cardiovascular tissue has been found to be remarkably useful in the clinical field. However, it goes without saying that a higher revascularization efficiency should be aimed for actual clinical application.

Patent Document 1: Japanese Kokai Publication 2001-78750 (JP-A 200178750)
Non-Patent Document 1: M L. Cooper, L. F. Hansbrough, R. L. Spielvogel et al., Biomaterials, 12: 243-248, 1991
Non-Patent Document 2: C. A. Vacanti, R. langer, et al., Plast. Reconstr. Surg, 88: 753-759, 1991

DISCLOSURE OF THE INVENTION

Problems to be Solved by the Invention

When a scaffold for culturing a cardiovascular tissue seeded with cells is transplanted, whether a blood vessel is regenerated or not depends on factors such as whether a sufficient amount of seeded cells are bound, and whether stenosis occurs until a blood vessel is regenerated. Since cells are usually seeded in the state of a suspension in which the cells are suspended in a culturing solution or the like, a scaffold for culturing cells is required to be flexible and have a high water absorption for highly efficient seeding. On the other hand, in order to avoid stenosis, possession of such a mechanical strength that a tubular body is less likely to collapse, that is, exertion of a high compressive elastic modulus and maintenance of an aperture are required when the tubular body is compressed. As described above, flexibility and high water absorbability, and a high compressive elastic modulus are in a relationship of trade-off, and are objects which are difficult to realize both of them.

An object of the present invention is to provide a scaffold for culturing a cardiovascular tissue which realizes a high seeding efficiency of cells and is less likely to collapse, and thereby can regenerate a blood vessel at an extremely high efficacy by cell seeding and transplantation. The present invention also provides a method of producing a cardiovascular tissue for transplantation using the same, a method of regenerating a cardiovascular tissue, and a cardiovascular tissue for transplantation.

Means for Solving the Problems

The present invention 1 is a scaffold for culturing a cardiovascular tissue, which is tubular, and comprises a foamed polymer comprising a bioabsorbable material reinforced with a reinforcing material comprising a bioabsorbable material, the foamed polymer comprising a lactide (D, L, DL isomer)-ε-caprolactone copolymer containing lactide (D, L, DL isomer) in a content of 50 to 54 mole % and ε-caprolactone in a content of 50 to 46 mole %, the reinforcing material being covered with the foamed polymer.

The present invention 2 is a scaffold for culturing a cardiovascular tissue, which is tubular, and comprises a foamed polymer comprising a bioabsorbable material reinforced with a reinforcing material comprising a bioabsorbable material, the foamed polymer having a thickness of 0.2 to 3.0 mm, the reinforcing material being situated at a center or on an outer plane of the scaffold, the foamed polymer being situated on an inner plane of the scaffold.

The present invention 3 is a scaffold for culturing a cardiovascular tissue, which is tubular, and comprises a foamed polymer comprising a bioabsorbable material reinforced with a reinforcing material comprising a bioabsorbable material, the reinforcing material comprising a bioabsorbable fiber coated with a bioabsorbable material, the reinforcing material being situated at a center or on an outer plane of the scaffold, the foamed polymer being situated on an inner plane of the scaffold.

The present invention 4 is a scaffold for culturing a cardiovascular tissue, which is tubular, and comprises a foamed polymer comprising a bioabsorbable material reinforced with a reinforcing material comprising a bioabsorbable material, the reinforcing material comprising a twisted yarn comprising a twisted bioabsorbable multifilament yarn, the reinforcing material being situated at a center or on an outer plane of the scaffold, and the foamed polymer being situated on an inner plane of the scaffold.

The present invention 5 is a scaffold for culturing a cardiovascular tissue, which is tubular, and comprises a foamed polymer comprising a bioabsorbable material reinforced with a reinforcing material comprising a bioabsorbable material, and a reinforcing yarn comprising a bioabsorbable material, the reinforcing yarn and the reinforcing material being situated at a center or on an outer plane of the foamed polymer, the foamed polymer being situated on an inner plane of the scaffold.

The present invention will be described in detail below.

The present inventors intensively studied and, as a result, found that, a scaffold for culturing a cardiovascular tissue, which is tubular, and comprises a foamed polymer comprising a bioabsorbable material reinforced with a reinforcing material comprising a bioabsorbable material obtained by a method using a lactide (D, L, DL isomer)-ε-caprolactone copolymer having a specific compositional ratio as a material for the foamed polymer (present invention 1), a method using a foamed polymer having a thickness in a specific range (present invention 2), a method using a bioabsorbable fiber coated with a bioabsorbable material as a material for the reinforcing material (present invention 3), a method using a reinforcing material comprising a twisted yarn (present invention 4), or a method in which the scaffold is further reinforced with a reinforcing yarn comprising a bioabsorbable material (present invention 5), realizes a high seeding efficiency of cells and is less likely to collapse, and thereby can regenerate a blood vessel at an extremely high efficiency by cell seeding and transplantation. Thus, the present inventors completed the present invention.

In the present description, the inventions are conveniently described as present inventions 1 to 5, but these may be implemented alone, or may be used in combination thereof.

The scaffold for culturing a cardiovascular tissue of the present invention is such that a foamed polymer comprising a bioabsorbable material is reinforced with a reinforcing material comprising a bioabsorbable material. By adopting such a structure, the foamed polymer functions as an anchorage to which a seeded cell can adhere firmly, and the reinforcing material plays a role of providing strength for withstanding a blood flow after transplantation for a term until a blood vessel is regenerated. In addition, since both of the foamed polymer and the reinforcing material comprise a bioabsorbable polymer, thereby, materials are absorbed after regeneration of a blood vessel, and it becomes unnecessary to continuously use an anti-coagulant or the like. Furthermore, since a regenerated blood vessel is an autologous tissue, growth is also expected.

In this respect, in the present description, examples of the cardiovascular tissue include a blood vessel, a heart valve, a pericardium and the like.

A pore size of the foamed polymer is required to be enough so that a seeded cell can be appropriately adhered and proliferate, and upon transplantation of the scaffold as a cardiovascular tissue, little blood leakage occurs. Specifically, the desirable lower limit is 5 μm, and the desirable upper limit is 100 μm. When the pore size is less than 5 μm, a seeded cell cannot enter a pore of the foamed polymer, and a sufficient seeding efficiency may not be obtained in some cases. When the pore size exceeds 100 μm, upon transplantation, blood leakage may occur in some cases. The more desirable lower limit is 10 μm, and the more desirable upper limit is 50 μm.

In addition, an average pore size of the fine pore can be measured by previously known methods such as a mercury pressing-in method and an image analyzing method.

The foamed polymer may be subjected to a hydrophilization treatment. By the hydrophilization treatment, when contacted with a cell suspension, the foamed polymer can rapidly absorb this, and cells can be more effectively and more uniformly seeded.

The hydrophilization treatment is not particularly limited, but examples include plasma treatment, glow discharge treatment, corona discharge treatment, ozone treatment, surface graft treatment, ultraviolet-ray irradiation treatment and the like. Among them, plasma treatment is desirable since a water absorption can be dramatically improved without changing an appearance of a scaffold for an artificial blood vessel.

The reinforcing material is not particularly limited as far as it has a higher strength than that of the foamed polymer, but examples include a fibrous body, a non-woven body, a film-form body and the like. Among them, a fibrous body comprising a bioabsorbable material such as a traverse knitted fabric, a longitudinal knitted fabric, a braid and a woven fabric is suitable.

In the scaffold for culturing a cardiovascular tissue of the present invention, it is desirable that the foamed polymer and the reinforcing material are incorporated.

A positional relationship between the foamed polymer and the reinforcing material is such that the reinforcing material is situated at a center or on an outer plane of a tubular body which is the scaffold for culturing a cardiovascular tissue of the present invention, and the foamed polymer is situated on an inner plane of the tubular body. In such a structure, the reinforcing material can sufficiently exert a role of providing strength, and regeneration of a blood vessel is progresses from its inner side to achieve early blood vessel regeneration.

An inner diameter and a length of the tubular body which is the scaffold for the culturing a cardiovascular tissue of the present invention may be selected in conformity with an objective blood vessel.

The desirable lower limit of a thickness of the scaffold for culturing a cardiovascular tissue of the present invention is 50 μm and the desirable upper limit is 5 mm. When the thickness is less than 50 μm, a sufficient strength for withstanding a blood flow may not be obtained, and suturing becomes difficult in some cases. When the thickness exceeds 5 mm, a time for absorption becomes longer without limitation, and this may be a cause for stenosis in some cases.

Examples of the bioabsorbable material constituting the foamed polymer, the reinforcing material and the reinforcing yarn include polyglycolic acid, polylactide (D, L, DL isomer), polycaprolactone, glycolic acid-lactide (D, L, DL isomer) copolymers, glycolic acid-ε-caprolactone copolymers, lactide (D, L, DL isomer)-ε-caprolactone copolymers, poly (p-dioxanone) and the like. These may be used alone, or two or more kinds thereof may be used in combination. Among these, the material is selected in every invention.

In the scaffold for culturing a cardiovascular tissue of the present invention 1, the foamed polymer comprises a lactide (D, L, DL isomer)-ε-caprolactone copolymer containing lactide (D, L, DL isomer) in a content of 50 to 54 mole %, and ε-caprolactone in a content of 50 to 46 mole %. By using the lactide (D, L, DL isomer)-ε-caprolactone copolymer having such a compositional ratio, flexibility and water absorbability enough to secure a sufficient number of the seeded cells, as well as a compressive elastic modulus high enough to avoid stenosis upon compression of the tubular body can be realized. When the content of the lactide (D, L, DL isomer) is less than 50 mole % (when the content of ε-caprolactone exceeds 50 mole %), a compressive elastic modulus upon compression of the tubular body is low, and stenosis may easily occur in some cases. When the content of the lactide (D, L, DL isomer) exceeds 54 mole % (the content of ε-caprolactone is less than 46 mole %), flexibility is not obtained, a water absorption becomes low, and a sufficient amount of cells cannot be seeded.

In the present description, a compositional ratio of the lactide (D, L, DL isomer)-ε-caprolactone copolymer may be such that, by using only one kind of copolymer, a compositional ratio of each component in the copolymer satisfies the above-described range, or by using a plurality of kinds of copolymers having different compositional ratios, a compositional ratio of each component as a whole of the plurality of kinds of copolymers satisfies the above-described range.

In the scaffold for culturing a cardiovascular tissue of the present invention 1, the reinforcing material comprises at least one kind selected from the group consisting of polyglycolic acid, polylactide (D, L, DL isomer), polycaprolactone, glycolic acid-lactide (D, L, DL isomer) copolymers, glycolic acid-ε-caprolactone copolymers, lactide (D, L, DL isomer)-ε-caprolactone copolymers and poly(p-dioxanone).

In the scaffold for culturing a cardiovascular tissue of the present invention 2, the lower limit of the thickness of the foamed polymer is 0.2 mm, and the upper limit thereof is 3.0 mm. By using the foamed polymer having such a thickness, flexibility and water absorbability enough to secure a sufficient number of seeded cells, as well as a compressive elastic modulus high enough to avoid stenosis upon compression of the tubular body can be realized. When the thickness is less than 0.2 mm, a compressive elastic modulus upon compression of the tubular body is low, and stenosis may easily occur in some cases. When the thickness exceeds 3.0 mm, flexibility is not obtained, a water absorption becomes low, and a sufficient amount of cells cannot be seeded.

In the scaffold for culturing a cardiovascular tissue of the present invention 2, a method of adjusting a thickness of the foamed polymer is not particularly limited, but examples include a method in which a concentration and an amount of a solution of a bioabsorbable material forming the foamed polymer is adjusted when the scaffold for culturing a cardiovascular tissue of the present invention is produced in a production process described later.

In the scaffold for culturing a cardiovascular tissue of the present invention 2, the foamed polymer and the reinforcing material comprise at least one kind selected from the group consisting of polyglycolic acid, polylactide (D, L, DL isomer), polycaprolactone, glycolic acid-lactide (D, L, DL isomer) copolymers, glycolic acid-ε-caprolactone copolymers, lactide (D, L, DL isomer)-ε-caprolactone copolymers and poly(p-dioxanone).

In the scaffold for culturing a cardiovascular tissue of the present invention 3, the reinforcing material comprises a bioabsorbable fiber coated with a bioabsorbable material. By using such a bioabsorbable fiber coated with a bioabsorbable material, flexibility and water absorbability enough to secure a sufficient number of seeded cells, as well as a compressive elastic modulus high enough to avoid stenosis upon compression of the tubular body can be realized.

The bioabsorbable fiber coated with the bioabsorbable material is not particularly limited, but a polyglycolic acid fiber coated with a lactide (D, L, DL isomer)-ε-caprolactone copolymer is suitable.

The coating method is not particularly limited, but examples include a method in which the polyglycolic acid fiber is immersed in a solution of the lactide (D, L, DL isomer)-ε-caprolactone copolymer, pulled out from the solution, and thereafter dried to form a reinforcing material, a method in which a reinforcing material is formed using a polyglycolic acid fiber, and thereafter immersed in a solution of the lactide (D, L, DL isomer)-ε-caprolactone copolymer, pulled out from the solution, and dried, and the like.

In the material for culturing a cardiovascular tissue of the present invention 3, the foamed polymer comprises at least one kind selected from the group consisting of polyglycolic acid, polylactide (D, L, DL isomer), polycaprolactone, glycolic acid-lactide (D, L, DL isomer) copolymers, glycolic acid-ε-caprolactone copolymers, lactide (D, L, DL isomer)-ε-caprolactone copolymers and poly(p-dioxanone).

In the scaffold for culturing a cardiovascular tissue of the present invention 4, the reinforcing material comprises a foamed polymer comprising a bioabsorbable material reinforced with a reinforcing material comprising a bioabsorbable material. By using such a twisted yarn, flexibility and water absorbability enough to secure a sufficient number of seeded cells, as well as a compressive elastic modulus high enough to avoid stenosis upon compression of the tubular body can be both realized.

Twisting of the twisted yarn is desirably such that S twisting is 350 T/m or more, and Z twisting is 220 T/m or more. Outside these ranges, the sufficient effect is not obtained in some cases.

In the scaffold for culturing a cardiovascular tissue of the present invention 4, the foamed polymer and the reinforcing material comprise at least one kind selected from the group consisting of polyglycolic acid, polylactide (D, L, DL isomer), polycaprolactone, glycolic acid-lactide (D, L, DL isomer) copolymers, glycolic acid-ε-caprolactone copolymers, lactide (D, L, DL isomer)-ε-caprolactone copolymers and poly(p-dioxanone).

In the scaffold for culturing a cardiovascular tissue of the present invention 5, a composite comprising the foamed polymer and the reinforcing material is further reinforced with a reinforcing yarn comprising a bioabsorbable material. By reinforcing with the reinforcing yarn, the scaffold for culturing a cardiovascular tissue of the present invention 5 can realize a high seeding efficiency of cells and is less likely to collapse, and thereby, a blood vessel can be regenerated at an extremely high efficiency by cell seeding and transplantation. The reinforcing yarn may be situated at a center of a foamed polymer, or may be situated on an outermost plane.

It is desirable that the reinforcing yarn is wound for a composite comprising the foamed polymer and the reinforcing material in a spiral form, a ring form or a X-shaped form. By disposition of the reinforcing yarn in such a manner, the resulting scaffold for culturing a cardiovascular tissue becomes much less likely to collapse.

In the scaffold for culturing a cardiovascular tissue of the present invention 5, it is desirable that the reinforcing yarn comprises at least one kind selected from the group consisting of poly-L-lactide, lactide (D, L, DL isomer)-ε-caprolactone copolymers and glycolic acid-ε-caprolactone copolymers.

The thickness of the reinforcing yarn used in the scaffold for culturing a cardiovascular tissue of the present invention 5 is not particularly limited, but the desirable lower limit of the cross-sectional diameter is 0.1 mm, and the desirable upper limit thereof is 1 mm. A reinforcing yarn having a cross-sectional diameter of less than 0.1 mm may fail to produce a sufficient reinforcing effect. Therefore, a scaffold using this reinforcing yarn may fail to maintain an aperture upon transplantation due to compression in the environment, resulting in stenosis or occlusion of the scaffold. A reinforcing yarn having a cross-sectional diameter exceeding 1 mm may cause hardening of the scaffold. The thickness of the reinforcing yarn may be represented according to USP suture thread thickness standard, that is, may be divided into groups such as 1-0 (cross-sectional diameter: 0.4 to 0.5 mm), 2-0 (cross-sectional diameter: 0.35 to 0.4 mm) and 3-0 (cross-sectional diameter: 0.25 to 0.3 mm).

A monofilament yarn is suitably used as the reinforcing yarn used in the scaffold for culturing a cardiovascular tissue of the present invention 5. Use of a monofilament yarn can produce a high reinforcing effect.

The method of producing the scaffold for culturing a cardiovascular tissue of the present invention is not particularly limited, but includes a method in which the reinforcing material having been prepared in advance is mounted in a mold, a solution of a bioabsorbable material for forming the foamed polymer is poured into the mold, and then freezed and lyophilized (lyophilization method), a method in which a mixed solution of a water-soluble substance and a bioabsorbable material for forming the foamed polymer is adhered to the reinforcing material having been prepared in advance, and then dried and the water-soluble substance is washed off by washing with water (dissolution out method), and the like. In the lyophilization method, foamed polymers having a variety of pore sizes can be prepared depending on a freezing temperature, a polymer concentration and the like. In the dissolution out method, a pore size of the foamed polymer can be controlled by adjusting particles of the water-soluble substance.

Then, a method for seeding cells on the scaffold for culturing a cardiovascular tissue of the present invention will be explained.

As cells to be seeded, common cell species are used for almost all cardiovascular tissues. That is, the cells is either of endothelial cells, bone marrow cells, smooth muscle cells, and fibroblasts, and usually, mixed cultured cells of these two or three kinds, or a monocyte component in bone marrow are seeded to perform tissue construction.

It is to be noted that the scaffold for culturing a cardiovascular tissue of the present invention can be transplanted without seeding cells.

Conditions for culturing cells used and a seeding method are shown below. The following A to C exemplify cell collection, culturing, and seeding method, respectively, upon preparation of a heart valve, a pericardium, and a blood vessel when mixed cultured cells are used, and D exemplifies a method when a bone marrow monocyte component is used.

A. Cell Isolation, Cell Culturing, Increase in Cell Number

A blood vessel tissue collected under complete cleanness is immersed in a cell culturing solution, and is washed using a phosphated saline in a clean bench. Then, the tissue is cut on a petri dish using a surgical knife according to simple explant technique. Fine tissue fragments having a size of about 1 to 2 $mm^2$ are evenly dispensed on the dish, and after about 20 minutes, the culturing solution is added after a tissue has adhered firmly to an underside of the dish. As the culturing solution, for example, Dulbecco's modified Eagle medium (DMEM) supplemented with 10% bovine fetal serum and 1% antibiotic solution (L-glutamine 29.2 mg/mL, penicillin G 1000 u/mL, streptomycin sulfate 10,000 μg/mL) is used. Blood vessel wall cells usually initiate to move from a tissue onto a dish after 5 to 7 days, and further after one week, a mixed cell colony is formed around the tissue fragment. After 2 to 3 weeks, mixed cells form the confluent state on the dish. Once the cells are in this state, the cells are immediately recovered with 0.25% trypsin, and are subcultured. Subculturing is performed, for example, on a 75 $cm^2$ culturing flask and, when this flask becomes almost confluent, about two million cells are obtained. Under the environment of 5% $CO_2$ and 21% $O_2$, subculturing is continued, and culturing is usually continued until around $10 \times 10^6$ cells are obtained. The culturing solution is exchanged every 4 to 5 days, and according to the result of pre-experiment, a cell doubling time is about 48 hours. In addition, counting of the number of cells during the elapse of time is performed according to a typical staining method with Trypan Blue.

B. Cell Separating, Endothelial Cell Purification

At a stage when mixed cells reach confluent, and a certain amount of cells are obtained, endothelial cells are selected and separated from mixed cells using FACS according to the following procedure. That is, for example, Dil-acetylated LDL (fluorescent dye marker) (hereinafter, referred to as Dil-Ac-LDL) of Biomedical Technology is added to a mixed cell culturing solution at a concentration of 1 μg/mL, and this is incubated for 24 hours. This marker is taken into a cell through a scavenger pathway peculiar to endothelial cells or macrophage. After 24 hours, a trypsin treatment is performed to make a mixed cell suspension, and this is sorted using a cell sorter (FACS machine: manufactured by Becton, Dickinson and Company). Cells are selected into Dil-Ac-LDL positive or negative based on its size and fluorescent emission. After separation, these are separately cultured, and culturing is continued until the number of endothelial cells reaches 2,000,000.

C. Tissue Construction

A first stage of constructing a tissue is in vitro cell seeding. Specifically, about 1,000,000/$cm^2$ Dil-Ac-LDL negative fibroblasts are seeded on the scaffold for culturing a cardiovascular tissue of the present invention. For 30 to 60 minutes immediately after fibroblast seeding, the cells are allowed to stand on a culturing dish in a clean bench, and thereafter, about 50 mL of a culturing solution is added. The culturing solution is fundamentally exchanged every day, and seven days later, that is, one day before surgical transplantation, a cell suspension (about 2,000,000 cells) of endothelial cells is further seeded, and conversion into a monolayer of endothelial cells is performed by this operation.

D. Collection and Seeding of Monocyte

As a method of collecting monocytes, first, on an operation day, after sedation and painkilling effects are obtained by general anesthesia, a bone marrow is collected from an iliac spine into a cylinder containing heparin for anti-coagulation using a bone marrow piercing needle by a clean procedure equivalent to a clean field at operation. In order to remove a bone fragment component, a fat component and a blood coagulating component from the obtained bone marrow, a bone marrow is first applied to a filter in a clean bench, this is calmly injected in an upper part of a gradient solution (e.g. trade name "Ficoll": manufactured by Pharmacia), and centrifuged. Thereafter, plasma components are separately fractionated under clean conditions, and a monocyte layer is separated. In order to obtain only a cell mass of the monocyte layer, centrifugation is further performed to obtain a cell mass of monocytes.

A size of the obtained cell mass is adjusted to a size of the scaffold for culturing a cardiovascular tissue to be seeded, diluted and stirred with an autoserum which has been appropriately fractionated, and is seeded on the scaffold for culturing a cardiovascular tissue by hand.

The scaffold for culturing a cardiovascular tissue after cell seeding is stored in an incubator at 37° C., 5% carbon dioxide and a humidity of 100% in the state it is immersed in autoserum until immediately before transplantation, in order to retain bone marrow monocyte cells.

A method of producing a cardiovascular tissue for transplantation comprising a scaffold with a surface covered with a cell, which comprises seeding a cell in vitro on the scaffold for culturing a cardiovascular tissue of the present invention, and further culturing the cell in vitro is also one of the present invention.

A method of regenerating a cardiovascular tissue, which comprises seeding a cell in vitro on the scaffold for culturing a cardiovascular tissue of the present invention, and further culturing the cell to regenerate a cardiovascular tissue in vitro is also one of the present inventions.

An endothelialized cardiovascular tissue for transplantation, which is obtained by seeding a cell in vitro on the scaffold for culturing a cardiovascular tissue of the present invention, and further culturing it in vitro is also one of the present inventions.

Since the cardiovascular tissue for transplantation of the present invention uses the scaffold for culturing a cardiovascular tissue of the present invention which realizes a high seeding efficiency of cells and is less likely to collapse, and thereby can regenerate a blood vessel at an extremely high efficiency by transplantation.

A method of transplanting the cardiovascular tissue for transplantation of the present invention is not particularly limited, but previously known methods can be used. By using an anti-thrombus drug, an anti-coagulant, an anti-platelet drug, a glucocorticoid drug (steroid drug), or a non-steroidal anti-inflammatory drug (NSAID) in combination, higher effects can be obtained. Among them, a glucocorticoid drug (steroid drug) affords the extremely high effect.

The anti-thrombus drug is not particularly limited, but examples include aspirin and the like.

The anti-coagulant is not particularly limited, but examples include heparin, warfarin, acenocoumarol, phenindione and the like.

The anti-platelet drug is not particularly limited, but examples include cilostazol, aspirin, ticlopidine and the like.

The glucocorticoid drug (steroid drug) is not particularly limited, but examples include predonisolone, dexamethasone, cortisol, and the like.

The non-steroidal anti-inflammatory drug (NSAID) is not particularly limited, but examples include aspirin, diclofenac, indometacin, ibuprofen, naproxen, and the like.

A method of using the glucocorticoid drug (steroid drug) or the like in combination is not particularly limited, but previously known methods can be used. For example, when the glucocorticoid drug (steroid drug) is used in combination, it is contemplated that after transplantation of the cardiovascular tissue for transplantation of the present invention, a glucocorticoid drug (steroid drug) is orally administered for a certain term.

Effects of the Invention

Accordingly, the present invention provides a scaffold for culturing a cardiovascular tissue, which can regenerate a blood vessel at an extremely high efficiency by cell seeding and transplantation, as well as a method of producing a cardiovascular tissue for transplantation using the same, a method of regenerating a cardiovascular tissue, and a cardiovascular tissue for transplantation.

BEST MODE FOR CARRYING OUT THE INVENTION

Hereinafter, the present invention will be described in detail by way of examples. However, the present invention is not limited only to these examples.

Experimental Example 1

An L-lactide-ε-caprolactone copolymer (molar ratio 50:50) and an L-lactide-ε-caprolactone copolymer (molar ratio 75:25) were mixed at a proportion of 100:0, 90:10, 80:20 or 70:30 to prepare L-lactide-ε-caprolactone copolymers in which L-lactide:ε-caprolactone (molar ratio) is 50:50, 52.5:47.5, 55:45 or 57.5:42.5, and 4 weight % dioxane solutions containing either of these was prepared.

A plain fabric obtained by knitting a 140 denier polyglycolic acid yarn into a cylinder was mounted on a bar made of Teflon (registered trademark) having an outer diameter of 12 mm, and this was immersed in any one of the L-lactide-ε-caprolactone copolymer solutions, frozen at −80° C., and lyophilized at −40° C. to 40° C. for 12 hours. Then, this was detached from the bar made of Teflon (registered trademark) with being inverted, and mounted on the bar made of Teflon (registered trademark) again, and the same procedure as that described above was performed to obtain a tubular scaffold for culturing a cardiovascular tissue having a sandwich structure reinforced with the glycolic acid knitted fabric. The thickness of a foamed layer (sponge layer) was about 1.3 mm as expressed by a sum of both sides.

The obtained scaffolds for culturing a cardiovascular tissue were evaluated in the following method.

Results are shown in Table 1.

(1) Compression Modulus Test

Regarding the obtained tubular scaffolds for culturing a cardiovascular tissue, a necessary strength for compressing each scaffold to ½ the diameter was obtained. When this value is large, it means that the scaffold has a high aperture diameter retaining force to stenosis.

(2) Stretch Test

Regarding the obtained tubular scaffolds for culturing a cardiovascular tissue, a maximum point strength when stretched in an outer diameter direction was obtained. When this value is great, it means that a strength to beat is great.

(3) Water Absorbing Test

Each of the obtained tubular scaffolds for culturing a cardiovascular tissue was cut into a size of 1 cm, which was used as a sample, and a weight thereof was measured. The sample was immersed into a physiological saline, and the sample was pushed with a finger 15 times to expel bubbles in the sample. After water was slightly removed, a weight after absorbing water was measured. From the weights before and after absorbing water, a water absorption was calculated. When this value is large, it means that an absorption amount of a cell suspension is large.

TABLE 1

| L-lactide:caprolactone (molar ratio) | Force necessary for ½ compression (g) | Maximum point strength at stretching (N) | Water absorption (%) |
|---|---|---|---|
| 50:50 | 7 | 72 | 380 |
| 52.5:47.5 | 12 | 65 | 275 |
| 55:45 | 14 | 68 | 205 |
| 57.5:42.5 | 23 | 86 | 150 |

Experimental Example 2

Using an L-lactide-ε-caprolactone copolymer (molar ratio 50:50), dioxane solutions containing the copolymer at four different concentrations of 2%, 4%, 6% and 8% were prepared.

The cylindrical knitted fabric having the same construction as that of Experimental Example 1 was mounted on a bar made of Teflon (registered trademark) having an outer diameter of 10 mm, and this was immersed into any one of the L-lactide-ε-caprolactone copolymer solutions, and thereafter, according to the same condition and procedure as those of Experimental Example 1, a tubular scaffold for culturing a cardiovascular tissue having a sandwich structure, which was reinforced with a glycolic acid knitted fabric, was obtained.

When a part of only a foamed polymer part of the respective obtained scaffolds for culturing a cardiovascular tissue was taken and measured, thickness thereof was 0.55 mm (2% concentration), 0.90 mm (4% concentration), 1.30 mm (6% concentration) and 2.10 mm (8% concentration), respectively.

The obtained scaffolds for culturing a cardiovascular tissue were evaluated according to the same manner as that of Experimental Example 1.

Results are shown in Table 2.

TABLE 2

| Foamed polymer thickness (mm) | Force necessary for ½ compression (g) | Water absorption (%) |
|---|---|---|
| 0.55 | 2 | 205 |
| 0.90 | 7 | 400 |
| 1.30 | 19 | 360 |
| 2.10 | 44 | 320 |

Experimental Example 3

A 4 weight % dioxane solution of an L-lactide-ε-caprolactone copolymer (molar ratio 50:50), and a 4 weight % dioxane solution of an L-lactide-ε-caprolactone copolymer (molar ratio 75:25) were prepared. Into each of these solutions was immersed a polyglycolic acid fiber of 140 denier, and the fiber was slowly taken out, and dried to obtain a polyglycolic acid fiber coated with the L-lactide-ε-caprolactone copolymer. The obtained coated polyglycolic acid fiber was used to make a cylindrical knitted fabric having the same knitting structure as that of Experimental Example 1, to obtain a reinforcing material.

This was mounted on the same bar made of Teflon (registered trademark) as that of Experimental Example 1 and, thereafter, according to the same condition and procedure as those of Experimental Example 1, a tubular scaffold for culturing a cardiovascular tissue of a sandwich structure, having a foamed layer of a thickness of 0.9 mm, wherein the foamed layer has a reinforcing material knitted with the coated polyglycolic acid knitted fabric, was obtained.

As a control, a non-coated polyglycolic acid fiber was used to prepare a reinforcing material, according to the similar manner, a scaffold for culturing a cardiovascular tissue was obtained.

The obtained scaffolds for culturing a cardiovascular tissue were evaluated according to the same manner as that of Experimental Example 1.

Results are shown in Table 3.

TABLE 3

| Coating (L-lactide:caprolactone) | Force necessary for ½ compression (g) | Maximum point strength at stretching (N) | Water absorption (%) |
|---|---|---|---|
| Nothing | 7 | 72 | 380 |
| 50:50 | 12 | 100 | 370 |
| 75:25 | 19 | 120 | 350 |

Experimental Example 4

In twisted yarns which is obtained by S-twisting a 140 denier multifilament yarn (35d/16 filaments) comprising polyglycolic acid one by one, bundling four yarns to make a bundling yarn, and further Z-twisting, three kinds of twisted yarns of low twisting (single yarn S twisting 120 T/m, bundling yarn Z twisting 75 T/m), intermediate twisting (single yarn S twisting 600 T/m, bundling yarn Z twisting 375 T/m) and high twisting (single yarn S twisting 1200 T/m, bundling yarn Z twisting 750 T/m) were obtained.

Each of the twisted yarns was knitted into a cylinder of the same kitting structure as that of Experimental Example 1, it was mounted on the same bar made of Teflon (registered trademark) as that of Experimental Example 1 and, thereafter, according to the same condition and procedure as those of Experimental Example 1, this was immersed into a 4 weight % dioxane solution of L-lactide-ε-caprolactone copolymer (molar ratio 50:50) to obtain a tubular scaffold for culturing a cardiovascular tissue of a sandwich structure, having a foamed layer of a thickness of 0.9 mm.

The obtained scaffolds for culturing a cardiovascular tissue were evaluated according to the same manner as that of Experimental Example 1.

Results are shown in Table 4.

TABLE 4

| Twisted yarn | Force necessary for ½ compression (g) | Water absorption (N) |
|---|---|---|
| Low twisting | 7 | 370 |
| Intermediate twisting | 20 | 400 |
| High twisting | 26 | 410 |

Experimental Example 5

A 4 weight % dioxane solution of an L-lactide-ε-caprolactone copolymer (molar ratio 50:50) was prepared.

A plain fabric obtained by knitting a 140 denier polyglycolic acid yarn into a cylinder was mounted on a bar made of Teflon (registered trademark) having an outer diameter of 10 mm, and this was immersed into the L-lactide-ε-caprolactone copolymer solution, frozen at −80° C., and lyophilized at −40° C. to 40° C. for 12 hours. Then, this was detached from the bar made of Teflon (registered trademark) with being inverted, and mounted again on the bar made of Teflon (registered trademark). On a surface thereof was wound a monofilament yarn (thickness, either of two kinds of 1-0 or 3-0) of an L-lactide-ε-caprolactone copolymer spirally at a pitch of 3 mm or 5 mm. This was immersed into the 4 weight % dioxane solution of the L-lactide-ε-caprolactone copolymer (molar ratio 50:50) for 30 seconds, frozen at −80° C., and lyophilized at −40° C. to 40° C. for 12 hours to obtain a scaffold for culturing a cardiovascular tissue of a sandwich structure, having a foamed layer of a thickness of 0.9 mm.

As a control, according to the same manner except that a monofilament yarn was not wound, a scaffold for culturing a cardiovascular tissue was obtained.

The obtained scaffolds for culturing a cardiovascular tissue were evaluated according to the same manner as that of Experimental Example 1.

Results are shown in Table 5.

TABLE 5

| Reinforcing yarn | Force necessary for ½ compression (g) | Water absorption (%) |
| --- | --- | --- |
| 1-0 yarn/3 mm pitch | 204 | 236 |
| 1-0 yarn/5 mm pitch | 127 | 284 |
| 3-0 yarn/3 mm pitch | 112 | 300 |
| 3-0 yarn/5 mm pitch | 60 | 318 |
| No reinforcing yarn | 7 | 353 |

The obtained scaffold for culturing a cardiovascular tissue with the 3-0 thickness yarn wound at a pitch of 3 mm was used for a transplantation experiment into dogs.

A bone marrow was taken from a femur head and an iliac head of each of seven dogs (beagles, weight about 10 kg) into a syringe containing heparin using a bone marrow piercing needle. In order to remove a bone fragment component, a fat component, and a blood coagulating component from the resulting bone marrow, the bone marrow was first applied to a filter in a clean bench, this was calmly injected in an upper part of a gradient solution (trade name "Ficoll": manufactured by Pharmacia), and this was centrifuged. Thereafter, plasma components were separately fractionated under clean conditions, and a monocyte layer was separated. In order to obtain only a cell mass of the monocyte layer, centrifugation was further performed to obtain a cell mass of the monocytes. The obtained cell mass was seeded on a scaffold for culturing a cardiovascular tissue which had been cut into a length of 3 cm, and this was transplanted into the inferior vena cava of the same dog.

All of the seven dogs were doing well after two months from the transplantation.

Experimental Example 6

A monofilament yarn (thickness 1-0) of a glycolic acid-ε-caprolactone copolymer (molar ratio; 75/25) was immersed into a 4 weight % dioxan solution of an L-lactide-ε-caprolactone copolymer (molar ratio 50:50), and then taken out slowly and dried. Thus, a glycolic acid-ε-caprolactone copolymer monofilament yarn coated with the L-lactide-ε-caprolactone copolymer was obtained.

A plain fabric obtained by knitting a 140 denier polyglycolic acid yarn into a cylinder was mounted on a bar made of Teflon (registered trademark) having an outer diameter of 10 mm, and this was immersed into an L-lactide-ε-caprolactone copolymer solution, frozen at −80° C., and lyophilized at −40° C. to 40° C. for 12 hours. Then, this was detached from the bar made of Teflon (registered trademark) with being inverted, and mounted again on the bar made of Teflon (registered trademark).

On a surface thereof was wound the obtained glycolic acid-ε-caprolactone copolymer monofilament yarn coated with the L-lactide-ε-caprolactone copolymer spirally at a pitch of 3 mm. This was immersed into the 4 weight % dioxane solution of the L-lactide-ε-caprolactone copolymer (molar ratio 50:50) for 30 seconds, frozen at −80° C., and lyophilized at −40° C. to 40° C. for 12 hours to obtain a scaffold for culturing a cardiovascular tissue of a sandwich structure, having a foamed layer of a thickness of 0.9 mm.

In the obtained scaffold for culturing a cardiovascular tissue, the foamed layer had a higher adhesion property to the monofilament yarn owing to the use of the glycolic acid-ε-caprolactone copolymer monofilament yarn coated with the L-lactide-ε-caprolactone copolymer. Therefore, the monofilament yarn was less likely to come off from the foamed layer.

Experimental Example 7

A 4 weight % dioxane solution of an L-lactide-ε-caprolactone copolymer (molar ratio 50:50) was prepared.

A plain fabric obtained by knitting a 140 denier polyglycolic acid yarn into a cylinder was mounted on a bar made of Teflon (registered trademark) having an outer diameter of 10 mm, and this was immersed into the L-lactide-ε-caprolactone copolymer solution, frozen at −80° C., and lyophilized at −40° C. to 40° C. for 12 hours. Then, this was detached from the bar made of Teflon (registered trademark) with being inverted, and mounted again on the bar made of Teflon (registered trademark). This was immersed into the L-lactide-ε-caprolactone copolymer solution, frozen at −80° C., and lyophilized at −40° C. to 40° C. for 12 hours. On a surface thereof was wound an L-lactide-ε-caprolactone copolymer monofilament yarn (thickness 1-0) spirally at a pitch of 3 mm. This was immersed into the 4 weight % dioxane solution of the L-lactide-ε-caprolactone copolymer (molar ratio 50:50) for 30 seconds, frozen at −80° C., and lyophilized at −40° C. to 40° C. for 12 hours to obtain a scaffold for culturing a cardiovascular tissue of a three-layer structure, having a foamed layer of a thickness of 0.9 mm.

The obtained scaffold for culturing a cardiovascular tissue could hold the reinforcing material more stably and firmly owing to its three-layer structure.

Reference Example

In twisted yarns which is obtained by S-twisting a 140 denier multifilament yarn (35d/16 filaments) comprising polyglycolic acid one by one, bundling four yarns to make a bundling yarn, and further Z-twisting, a twisted yarn of low twisting (single yarn S twisting 120 T/m, bundling yarn Z twisting 75 T/m) was obtained.

The obtained twisted yarn of low twisting was knitted into a cylinder of the same knitting structure as that of Experimental Example 1, it was mounted on the same bar made of Teflon (registered trademark) as that of Experimental Example 1, and thereafter, according to the same condition and procedure as those of Experimental Example 1, this was immersed into a 4 weight % dioxane solution of an L-lactide-ε-caprolactone copolymer (molar ratio 50:50) to obtain a tubular scaffold for culturing a cardiovascular tissue of a sandwich structure, having a foamed layer of a thickness of 0.9 mm.

A bone marrow was taken from a femur head and an iliac head of each dog (beagles, weight about 10 kg) into a syringe containing heparin using a bone marrow piercing needle. In order to remove a bone fragment component, a fat component, and a blood coagulating component from the resulting bone marrow, the bone marrow was first applied to a filter in a clean bench, this was calmly injected in an upper part of a gradient solution (trade name "Ficoll": manufactured by Pharmacia), and this was centrifuged. Thereafter, plasma components were separately fractionated under clean conditions, and a monocyte layer was separated. In order to obtain only a cell mass of the monocyte layer, centrifugation was further performed to obtain a cell mass of the monocytes. The obtained cell mass was seeded on a scaffold for culturing a cardiovascular tissue which had been cut into a length of 3 cm, this was transplanted into the inferior vena cava of the same dog. The dogs were divided into a group to which 0.5 mg/kg prednisolone which is a glucocorticoid drug (steroid drug) was administered by mixing into a feed for one month after operation, or a group to which no drug was administered (3 dogs in both groups).

As a result, in the prednisolone-administered group, increase in leukocyte could be suppressed, and an inflammatory reaction could be suppressed.

INDUSTRIAL APPLICABILITY

The present invention provides a scaffold for culturing a cardiovascular tissue, which can regenerate a blood vessel at an extremely high efficiency by cell seeding and transplantation, as well as a method of producing a cardiovascular tissue for transplantation using the same, a method of regenerating a cardiovascular tissue, and a cardiovascular tissue for transplantation.

The invention claimed is:

1. A scaffold for culturing a cardiovascular tissue,
    which is tubular, and comprises a foamed polymer comprising a bioabsorbable material reinforced with a reinforcing material comprising a bioabsorbable material,
    the reinforcing material comprising a twisted yarn comprising a twisted bioabsorbable multifilament yarn,
    the reinforcing material being situated at a center or on an outer plane of the scaffold, and
    the foamed polymer being situated on an inner plane of the scaffold.

2. A method of producing a cardiovascular tissue for transplantation comprising a scaffold having a surface covered with a cell,
    which comprises seeding a cell in vitro on the scaffold for culturing a cardiovascular tissue according to claim 1, and further culturing the cell in vitro.

3. A method of regenerating a cardiovascular tissue,
    which comprises seeding a cell in vitro on the scaffold for culturing a cardiovascular tissue according to claim 1, and further culturing the cell to regenerate a cardiovascular tissue in vitro.

4. A cardiovascular tissue for transplantation,
    which is obtained by seeding an endothelial cell, a marrow cell, a smooth muscle cell or a fibroblast in vitro on the scaffold for culturing a cardiovascular tissue according to claim 1, and further culturing the cell in vitro.

5. A scaffold for culturing a cardiovascular tissue,
    which is tubular, and comprises a foamed polymer comprising a bioabsorbable material reinforced with a reinforcing material comprising a bioabsorbable material, and a reinforcing yarn comprising a bioabsorbable material,
    the reinforcing yarn and the reinforcing material being situated at a center or on an outer plane of the foamed polymer,
    the foamed polymer being situated on an inner plane of the scaffold, and
    the reinforcing yarn being wound in a spiral form, a ring form, or a X-shaped form
    wherein the reinforcing yarn is a monofilament yarn having a cross-sectional diameter of 0.1 mm to 1 mm.

6. The scaffold for culturing a cardiovascular tissue according to claim 5,
    wherein the reinforcing yarn comprises at least one kind of compound selected from the group consisting of poly-L-lactide, a lactide ε-caprolactone copolymer and a glycolic acid-ε-caprolactone copolymer.

7. A method of producing a cardiovascular tissue for transplantation comprising a scaffold having a surface covered with a cell,
    which comprises seeding a cell in vitro on the scaffold for culturing a cardiovascular tissue according to claim 5, and further culturing the cell in vitro.

8. A method of regenerating a cardiovascular tissue,
    which comprises seeding a cell in vitro on the scaffold for culturing a cardiovascular tissue according to claim 5, and further culturing the cell to regenerate a cardiovascular tissue in vitro.

9. A cardiovascular tissue for transplantation,
    which is obtained by seeding an endothelial cell, a marrow cell, a smooth muscle cell or a fibroblast in vitro on the scaffold for culturing a cardiovascular tissue according to claim 5, and further culturing the cell in vitro.

* * * * *